US012582705B2

(12) United States Patent
Kang et al.

(10) Patent No.: US 12,582,705 B2
(45) Date of Patent: Mar. 24, 2026

(54) COMPOSITION COMPRISING BOTULINUM TOXIN OR SALT THEREOF FOR INCREASING ENDOMETRIAL BLOOD FLOW RATE

(71) Applicant: CHA UNIVERSITY INDUSTRY-ACADEMIC COOPERATION FOUNDATION, Pocheon-si (KR)

(72) Inventors: Youn Jung Kang, Yongin-si (KR); Hwa Seon Koo, Sejong-si (KR); Jung Jae Ko, Yongin-si (KR)

(73) Assignee: CHA UNIVERSITY INDUSTRY-ACADEMIC COOPERATION FOUNDATION, Pocheon-si (KR)

( * ) Notice: Subject to any disclaimer, the term of this patent is extended or adjusted under 35 U.S.C. 154(b) by 786 days.

(21) Appl. No.: 17/773,391

(22) PCT Filed: Apr. 28, 2020

(86) PCT No.: PCT/KR2020/005626
§ 371 (c)(1),
(2) Date: Apr. 29, 2022

(87) PCT Pub. No.: WO2021/085769
PCT Pub. Date: May 6, 2021

(65) Prior Publication Data
US 2022/0409706 A1 Dec. 29, 2022

(30) Foreign Application Priority Data
Oct. 31, 2019 (KR) ......................... 10-2019-0138207

(51) Int. Cl.
*A61K 38/48* (2006.01)
*A61P 15/08* (2006.01)

(52) U.S. Cl.
CPC .......... *A61K 38/4893* (2013.01); *A61P 15/08* (2018.01)

(58) Field of Classification Search
CPC ...... A61K 38/4893; A61K 38/48; A61P 15/08
See application file for complete search history.

(56) References Cited

U.S. PATENT DOCUMENTS

| | | |
|---|---|---|
| 7,429,386 B2 | 9/2008 | First |
| 8,071,550 B2 | 12/2011 | Schiffman |
| 10,925,837 B2 | 2/2021 | Park et al. |
| 2004/0175399 A1 | 9/2004 | Schiffman |
| 2008/0292612 A1 | 11/2008 | Berruet |
| 2011/0142882 A1 | 6/2011 | Koman et al. |
| 2012/0039940 A1 | 2/2012 | Schiffman |
| 2013/0078295 A1 | 3/2013 | Cebrian Puche et al. |

FOREIGN PATENT DOCUMENTS

| | | | |
|---|---|---|---|
| CN | 103096980 B | 2/2018 | |
| EP | 2 161 033 B1 | 5/2013 | |
| KR | 10-2007-0019141 A | 2/2007 | |
| KR | 10-2008-0086522 A | 9/2008 | |
| KR | 10-2009-0009539 A | 1/2009 | |
| KR | 10-2019-0042020 A | 4/2019 | |
| WO | WO 2004/078202 A1 | 9/2004 | |
| WO | WO 2007/085728 A2 | 8/2007 | |
| WO | WO-2010101968 A1 * | 9/2010 | ......... A61K 38/4886 |

OTHER PUBLICATIONS

Japanese Office Action issued on Jun. 6, 2023 in Japanese Patent Application No. 2022-525195 (with English translation), 6 pages.
Sato et al., "The Hemodynamic Change of Botulinum Toxin Type a On Femoral Artery in the Rat", Journal of the Pharmaceutical Affairs, 2012, vol. 72, No. 3, pp. 336-341 (with English Abstract).
Korean Office Action issued Feb. 23, 2023 in Korean Patent Application No. 10-2019-0138207 (with English language translation), 14 pages.
Australian Examination Report issued Feb. 22, 2024 in Australian Patent Application No. 2020374555, 8 pages.
Wang et al., "Role of endometrial blood flow assessment with color Doppler energy in predicting pregnancy outcome of IVF-ET cycles", Reproductive Biology and Endocrinology, vol. 8, No. 122, Oct. 2010, 7 pages.
Kim et al., "Relationship between endometrial and subendometrial blood flow measured by three-dimensional power Doppler ultrasound and pregnancy after intrauterine insemination", Fertility and Sterility, vol. 94, No. 2, Jul. 2010, pp. 747-752 (total 6 pages).
Sardana et al., "Correlation of subendometrial-endometrial blood flow assessment by two-dimensional power Doppler with pregnancy outcome in frozen-thawed embryo transfer cycles", Journal of Human Reproductive Sciences, vol. 7, Issue 2, Apr. 2014, pp. 130-135 (total 6 pages).
Australian Office Action issued Aug. 27, 2024 in Australian Patent Application No. 2020374555, 3 pages.
International Search Report issued on Aug. 12, 2020 in PCT/KR2020/005626 filed on Apr. 28, 2020, 4 pages.
Mitchell F. Brin et al., "Pregnancy outcomes following exposure to onabotulinumtoxinA", pharmacoepidemiology and drug safety, vol. 25, 2016, pp. 179-187.

(Continued)

*Primary Examiner* — Kade Ariani
(74) *Attorney, Agent, or Firm* — Oblon, McClelland, Maier & Neustadt, L.L.P.

(57) ABSTRACT

A composition may increase a rate of endometrial blood flow and a composition for increasing implantation potential, including botulinum toxin or a salt thereof, and a pharmaceutical composition may preventing or treating subfertility or infertility, including botulinum toxin or a pharmaceutically acceptable salt thereof. Such compositions can increase a rate of endometrial blood flow and improve embryonic implantation potential just by being applied to the endometrium, and thus may be helpful to patients with subfertility or infertility, especially those who have repetitive failures in embryonic implantation. Since the compositions include botulinum toxin which is a substance that has been widely applied to the human body for cosmetic purposes, studies on human toxicity may have a shortened period, and thus the disclosure is very useful in economical and industrial aspects.

15 Claims, 7 Drawing Sheets

(56)                         References Cited

OTHER PUBLICATIONS

Peter B. Arnold et al., "Modification of Blood Vessel Diameter Following Perivascular Application of Botulinum Toxin-A", Hand, vol. 4, 2009, pp. 302-307.

Ralf L. Schild et al., "Endometrial receptivity in an in vitro fertilization program as assessed by spiral artery blood flow, endometrial thickness, endometrial volume and uterine artery blood flow", Fertility and Sterility, vol. 75, No. 2, 2001, pp. 361-366.

Kang, Y.-J. et al., The impact of Botulinum Toxin a (BoTA) treatment on endometrial blood flow. ASRM Abstracts, vol. 112, No. 3, Supplement, 2019, p. e246, (2 total pages).

Kang, Y.-J et al., "The impact of Botulinum Toxin A (BoTA) treatment on endometrial blood flow", American Journal of Reproductive Immunology, vol. 81, Supplement 1, 2019, pp. 40-40 (1).

Jia-Peng He et al. "Identification of Gene Expression Changes Associated With Uterine Receptivity in Mice," Frontiers in Physiology, vol. 10, Article 125, 2019, 1-11.

Michael Tan et al., "Botulinum toxin type A in pregnancy," Motherisk Update, Canadian Family Physician, vol. 59, 2013, pp. 1183-1184.

Botox, No Longer Just Cosmetic but an Aid in Possible Treatment of Endometriosis: Medicine & Health: Science Times, 2019, https://www.sciencetimes.com/articles/23464/20190726/botox-no-longer-just-cosmetic-but-an-aid-in-possible-treatment-of-endometriosis.htm, (2 pages).

* cited by examiner

FIG. 1

Angiogenesis

| Filter: 10 | Fold change | P-value | |
|---|---|---|---|
| Gene symbol | BotoxDay8 / Control | BotoxDay8 / Control | Description |
| Ccl7 | 7.979 | 0.029 | chemokine (C-C motif) ligand 7 |
| Cyr61 | 4.683 | 0.004 | cysteine rich protein 61 |
| Itgb3 | 2.894 | 0.02 | integrin beta 3 |
| Foxc1 | 2.803 | 0.001 | forkhead box C1 |
| Clec14a | 2.779 | 0.034 | C-type lectin domain family 14, member a |
| Hif3a | 2.153 | 0.049 | hypoxia inducible factor 3, alpha sub unit |
| Gpx1 | 2.125 | 0.026 | glutathione peroxidase 1 |
| Cd34 | 2.047 | 0.038 | CD34 antigen |
| Ccbe1 | 0.448 | 0.018 | collagen and calcium binding EGF domains 1 |
| Tgfbi | 0.326 | 0.015 | transforming growth factor, beta induced |

FIG. 2

Embryo implantation

| Filter: 4. | Fold change | P-value | |
|---|---|---|---|
| Gene symbol | BotoxDay8 / Control | BotoxDay8 / Control | Description |
| Lif | 4.021 | 0.008 | leukemia inhibitory factor |
| Itgb3 | 2.894 | 0.002 | integrin beta 3 |
| Stc2 | 2.522 | 0.033 | stanniocalcin 2 |
| Stc1 | 0.447 | 0.018 | stanniocalcin 1 |

Saline-
treated
BoTA-
treated
Saline-
treated
BoTA-
treated

COMPOSITION COMPRISING BOTULINUM TOXIN OR SALT THEREOF FOR INCREASING ENDOMETRIAL BLOOD FLOW RATE

CROSS-REFERENCE TO RELATED APPLICATIONS

The present application is the national stage of international application PCT/KR2020/005626, filed on Apr. 28, 2020, and claims the benefit of the filing date of Korean Appl. No. 10-2019-0138207, filed on Oct. 31, 2019.

STATEMENT REGARDING PRIOR DISCLOSURES BY THE INVENTOR OR A JOINT INVENTOR

Aspects of this application were disclosed in Kang et al., "The impact of Botulinum Toxin A (BoTA) treatment on endometrial blood flow," ASMR Abstracts (Supplement) 2019, 112(3), P03.

TECHNICAL FIELD

The present disclosure relates to a composition including botulinum toxin or a salt thereof for increasing a rate of endometrial blood flow.

BACKGROUND ART

As the subfertile population increases, in-vitro fertilization is being performed relatively actively, but the success rate does not exceed 50%. Even though many researchers are striving to improve the success rate of in-vitro fertilization, pregnancy failure due to repeated failures of implantation even when quality embryos are transplanted and a thin endometrium with which it is difficult to provide an appropriate environment for pregnancy still remain unsolved issues of in-vitro fertilization. Recurrent pregnancy loss, which is habitual miscarriage after successful implantation, is also pregnancy failure due to endometrial factors.

In order to solve this, many researchers are experimentally applying many substances, but there are no substances of which the mechanism is clearly revealed or the effect is proven. Therefore, the development and discovery of safe substances with proven effects are desperately needed.

DESCRIPTION OF EMBODIMENTS

Technical Problem

An aspect is to provide a composition including botulinum toxin or a salt thereof for increasing a rate of endometrial blood flow increasing a rate of endometrial blood flow.

Another aspect is to provide a composition including botulinum toxin or a salt thereof for improving implantation potential.

Still another aspect is to provide a pharmaceutical composition including botulinum toxin or a pharmaceutically acceptable salt thereof for prevention or treatment of subfertility or infertility.

Still another aspect is to provide a method of preventing or treating subfertility or infertility including administering the pharmaceutical composition to a subject with subfertility or infertility.

Solution to Problem

An aspect provides a composition including botulinum toxin or a salt thereof for increasing a rate of endometrial blood flow increasing a rate of endometrial blood flow.

The botulinum toxin is a neurotoxic protein that is produced by *Clostridium botulinum* bacteria. More than 127 species belong to *Clostridium* genus and are classified according to the form and function. Anaerobic, Gram-positive bacteria *Clostridium botulinum* produces botulinum toxin which is a powerful polypeptide neurotoxin that causes a neuroparalysis disease called botulism in humans and animals.

The botulinum toxin may be at least one botulinum toxin selected from serotype A, B, C1, D, E, F, and G that are classified by neutralizing with type-specific antibodies, and specifically, may be botulinum toxin A.

The botulinum toxin A is one of the most fatal natural biologics known to humans, and lethal dose 50 (LD50) of the commercially available botulinum toxin type A (purified neurotoxin complex) is about 50 picograms (i.e., one unit).

1 unit of the botulinum toxin may be defined as LD50 intraperitoneally injected to female Swiss Webster mice each weighing about 18 g to 20 g.

A molecular weight of the botulinum toxin of all known 7 serotypes is about 150 kD. Botulinum toxins may be released by *Clostridium* bacteria, as a complex containing 150 kD botulinum toxin protein molecules with associated non-toxic proteins. A botulinum toxin type A complex may be generated by *Clostridium* bacteria as 900 KD, 500 KD, and 300 kD types. Botulinum toxin types B and C1 may be generated as a 700 kD or 500 kD complex, and botulinum toxin type D may be generated as 300 kD and 500 kD complexes. Lastly, botulinum toxin types E and F may be generated as complexes of about 300 kD. The complexes (i.e., having a molecular weight greater than about 150 kD) may include non-toxic erythrocytic hemagglutinin proteins and non-toxic non-erythrocytic haemagglutinin proteins. These two non-toxic proteins (included in the related neurotoxin complex with a botulinum toxin molecule) may provide stability to botulinum toxin molecules against denaturation.

The botulinum toxin may be derived from the nature or may be synthesized by using a known organic synthesis method, and may be non-protein compounds, peptides, tissues derived from plants, extracts of cells, or products of culturing microorganisms (for example, bacteria, fungi, or particularly, yeast).

Specifically, from the Hall A Strain of *Clostridium botulinum*, crystalline botulinum toxin type A of a good quality may be obtained, which has a specific effect of $3 \times 10^7$ U/mg or more, A260/A278 is 0.60 or less, and exhibits a characteristic band pattern in gel electrophoresis. Shantz Process known in the art may be used to obtain crystalline botulinum toxin type A. A botulinum toxin type A complex may be separated and purified from anaerobically fermented product of *Clostridium botulinum* type A cultured in an appropriate medium. Such a known process may be used to isolate and obtain pure botulinum toxins from non-toxic proteins, for example, to purify botulinum toxin type A which has a molecular weight of about 150 kD and a specific effect of $1 \times 10^8$ LD50 U/mg to $2 \times 10^8$ LD50 U/mg or more; to purify botulinum toxin type B which has a molecular weight of about 156 kD and a specific effect of $1 \times 10^8$ LD50 U/mg to $2 \times 10^8$ LD50 U/mg or more; or to purify botulinum toxin type F which has a molecular weight of about 155 kD and a specific effect of $1 \times 10^7$ LD50 U/mg to $2 \times 10^7$ LD50 U/mg or more.

The botulinum toxin and/or a botulinum toxin complex is commercially available from a chemical manufacturer known in the art, and pure botulinum toxins may also be used.

As used herein, the term "salt" refers to a salt prepared by using a relatively non-toxic acid or base and the specific compound according to an aspect. When the compound includes a relatively acidic functional group, a sufficient amount of a base in a pure solution or a suitable inert solvent may be made to contact a neutral form of the compound to obtain a base addition salt. The base addition salt includes salts of sodium, potassium, calcium, ammonium, organic amine, magnesium, or similar salts thereto. When the compound includes a relatively basic functional group, a sufficient amount of an acid in a pure solution or a suitable inert solvent may be made to contact a neutral form of the compound to obtain an acid addition salt. The acid addition salt includes salts of inorganic acids such as hydrochloric acid, hydrobromic acid, nitric acid, carbonate, hydrogencarbonate ion, phosphoric acid, monohydrogen phosphate, dihydrogen phosphate, sulfuric acid, hydrogen sulfate ion, hydroiodic acid, or phosphonic acid; organic acids such as, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid, methanesulfonic acid; and further includes salts of amino acids (eg, arginine, etc.) and salts of organic acids such as glucuronic acid.

The salt may be synthesized by a chemical method in the art from a mother compound including an acidic or basic moiety. In general, such a salt is prepared by reacting stoichiometric amount of a base or acid with a free acid or base of these compounds in an aquatic or organic solvent, or a mixture thereof. Generally, a non-aqueous medium such as ether, ethyl acetate, ethanol, isopropanol or acetonitrile is preferable.

The composition may increase angiogenesis of the endometrium and may increase endometrial blood flow rate or receptivity.

The term "endometrial cells" refers to cells located in the mucosa that covers the inner wall of the uterus, and a layer in which a fertilized egg is implanted and developed to be an embryo and a placenta is formed.

The botulinum toxin or a salt thereof may increase expression of at least one gene selected from Ccl7, Cyr61, Itgb3, Foxc1, Clec14a, Hif3a, Gpx1, Cd34, Lif, Itgb3, Stc2, Dll1, Cd160, Calca and Cd31, which are markers related to endometrial angiogenesis or embryo transplant.

In addition, the botulinum toxin or a salt thereof may decrease expression of at least one gene selected from Ccbe1, Tgfbi, Stc1, Adra2b and Tbx4, which are markers related to angiogenesis of the endometrium or embryo transplant.

The concentration of the botulinum toxin or a salt thereof in the composition may be 0.01 unit to 2 unit, specifically, 0.1 unit to 1 unit, or more specifically, 0.3 unit to 0.7 unit. When the concentration of botulinum toxin is within the range, angiogenesis of the endometrium is maximally increased, and endometrial blood flow and receptivity may be maximally increased.

Another aspect provides a composition including botulinum toxin or a salt thereof for improving embryonic implantation potential.

The "botulinum toxin" or "salt" may be included in the above-described range, specifically, the botulinum toxin may be at least one botulinum toxin selected from serotypes A, B, C1, D, E, F, and G that are classified by neutralizing with type-specific antibodies, more specifically, may be botulinum toxin A.

In addition, the concentration of the botulinum toxin or a salt thereof in the composition may be 0.01 unit to 2 unit, specifically, 0.1 unit to 1 unit, or more specifically, 0.3 unit to 0.7 unit. When the concentration of the botulinum toxin is within the range, angiogenesis of the endometrium is maximally increased, endometrial blood flow rate and receptivity may be maximally increased, and thus implantation potential may be maximally increased.

The composition may increase angiogenesis of the endometrium and may increase endometrial blood flow rate or receptivity to improve implantation potential.

The term, "improvement of implantation potential" may mean promotion of implantation in the uterus of a fertilized egg which is an egg that is fused with a sperm and development thereof into a fetus, specifically, the term may mean promotion of implantation of a fertilized egg in the uterus or increasing the implantation probability to promote pregnancy.

In addition, the term "fertilized embryo" refers to a zygote which is an egg fused to a sperm that has undergone at least one cell division until it becomes a complete entity in early stages of development, specifically, a fertilized embryo in a test tube, but is not limited thereto. In the present disclosure, the term "implantation" refers to a state that a fertilized embryo adheres to the wall of the uterus so that the fetus can receive oxygen and nutrients from the mother's body.

Still another aspect provides a pharmaceutical composition including botulinum toxin or a pharmaceutically acceptable salt thereof for prevention or treatment of subfertility or infertility.

The botulinum toxin may be at least one botulinum toxin selected from serotypes A, B, C1, D, E, F, and G that are classified by neutralizing with type-specific antibodies, and specifically, may be botulinum toxin A.

In addition, the "botulinum toxin", "salt", and the like may be within the above range, and the term "pharmaceutically acceptable" means exhibiting a characteristic of not being toxic to the cells or humans exposed to the composition.

The pharmaceutical composition may increase angiogenesis in the endometrium and thus may increase endometrial blood flow rate or receptivity to improve embryonic implantation potential. Accordingly, the pharmaceutical composition may exhibit a therapeutic effect of preventing or treating subfertility or infertility due to problems in embryonic implantation.

The subfertility or infertility be may due to at least one selected from damaged endometrium, hypofunction of the uterus, recurrent pregnancy loss, recurrent failure of implantation of unknown cause, and failure of implantation due to a thin endometrium.

The term, "subfertility or infertility" refers to a state of a couple failing to reach a pregnancy within 1 year of regular unprotected sexual intercourse, and the subfertility or infertility may be due to non-implantation of ovum or female infertility of uterine origin, or more specifically, due to at least one selected from damaged endometrium, hypofunction of the uterus, recurrent pregnancy loss, recurrent failure of implantation of unknown cause, and failure of implantation due to a thin endometrium, although not limited thereto.

The term "damaged endometrium" refers to destruction of the normal integrity of the entire endometrium or a part of the tissue structure caused by a uterine surgery, tuberculosis infection, physical damage or endometrial infection, and includes "wound", "lesions" "necrosis", "ulcer", and the like. A damaged endometrium may bring about hypofunction of the uterus, failure of embryo implantation, and abnormal embryonic development, causing subfertility or infertility.

In addition, the term "recurrent pregnancy loss" refers to a reproductive disease affecting 2% to 5% of pregnant women, and is defined as at least three consecutive pregnancy losses prior to 20th week to 28th week of pregnancy.

The term "prevention" may refer to all acts of inhibiting or delaying subfertility or infertility of a subject by administering a pharmaceutical composition according to an aspect.

The term "treatment" may refer to all acts that cause symptoms of subfertility or infertility of a subject to be improved or advantageously altered by administering a pharmaceutical composition according to an aspect.

The pharmaceutical composition may include active ingredients only, or may include at least one pharmaceutically acceptable carrier, excipient or diluent to be provided as a pharmaceutical composition.

Specifically, the carrier may be, for example, a colloidal suspension, powder, saline, lipid, liposome, microspheres or nano spherical particles. The carrier may form a complex with a conveying means or may be related to a conveying means, and may be carried in the body by using a transportation system known in the art such as lipids, liposomes, fine particles, gold, nanoparticles, polymers, condensation reactants, polysaccharides, polyamino acids, dendrimers, saponins, adsorption enhancers, or fatty acids.

When the pharmaceutical composition is formulated, the composition may be prepared by using diluents or excipients such as lubricants, sweeteners, flavoring agents, emulsifiers, suspending agents, preservatives, fillers, extenders, binders, wetting agents, disintegrants, and surfactants. Solid formulations for oral administration may include tablets, pills, powders, granules, capsules, and the like, and such solid formulations may be prepared by mixing the composition with at least one excipient such as, starch, calcium carbonate, sucrose, lactose, gelatin, and the like. In addition to a simple excipient, lubricants such as magnesium stearate and talc may also be used. Liquid formulations for oral administration may include a suspension, oral liquid, emulsion, and syrup, and apart from simple diluents such as water and liquid paraffin, various excipients, for example, wetting agents, sweetening agents, flavoring agents, preservatives, etc. may be included. Formulations for parenteral administration may include sterile aqueous solutions, non-aqueous solvents, suspensions, emulsions, freeze-dried formulations, and suppositories. For non-aqueous solvents and suspensions, vegetable oils such as propyleneglycol, polyetheyleneglycol, olive oil; and injectable ester such as ethyloleate may be used. As substrates for suppositories, witepsol, macrogol, tween 61, cacao butter, laurin oil, and glycerogelatin may be used, and when prepared in the form of an eye drop, diluents or excipients known in the art may be used.

In addition, the pharmaceutical composition may be administered in combination with subfertility or infertility medicines in the art, that is, provided by mixing with a composition for preventing or treating subfertility or infertility known in the art.

The pharmaceutical composition may be administered in parallel with a known composition having a preventive or therapeutic effect for subfertility or infertility, and may be administered simultaneously, separately, or sequentially, or may be administered in a single dose or in multiple doses. Administration of an amount that results in the maximum effect without side effects is important in consideration of all of the above elements, and the amount may be easily determined by those skilled in the art.

The term "administration" means introducing a predetermined substance to a subject, and "subject" includes all organisms that may have infertility including a human, mouse, livestock, etc. Specifically, the subject may be a mammal including human.

In an aspect, administration routes of the pharmaceutical composition includes, oral, intravenous, intramuscular, intra-arterial, intramedullary, intradural, intracardiac, percutaneous, subcutaneous, intraperitoneal, intranasal, intraintestinal, local, sublingual, or intrarectal, although not limited thereto.

The composition may be administered orally or parenterally, and when administered parenterally, external dermal application, intraperitoneal injection, intrarectal injection, subcutaneous injection, intravenous injection, intramuscular injection or intrathoracic injection may be selected. Specifically, the composition may be administered as an external dermal application by applying on the endometrium, or the composition may be directly injected to the endometrium in the form of an injection. More specifically, the pharmaceutical composition may be applied to the endometrium of a subject.

The pharmaceutical composition is administered in a pharmaceutically effective amount. The term "pharmaceutically effective amount" refers to an amount that is sufficient to treat a disease with a reasonable benefit/risk ratio applicable to a medical treatment, and the effective amount may be determined depending on the factors including type and severity of the patient's disease, drug activity, sensitivity to the drug, duration and route of administration, excretion rate, treatment period, simultaneously administered drugs, and other well-known factors in the medical field. The administration may be performed once a day or several times a day in allocations.

Specifically, the effective amount of the pharmaceutical composition may vary depending on the patient's age, state, body weight, absorption rate of active ingredients in the body, inactivation rate, excretion rate, the type of the disease, and simultaneously administered drugs, and the amount may be increased or decreased depending on the administration route, severity of obesity, sex, body weight, age, etc.

The concentration of the botulinum toxin or a salt thereof in the composition may be 0.01 unit to 2 unit, specifically, 0.1 unit to 1 unit, or more specifically, 0.3 unit to 0.7 unit. When the concentration of botulinum toxin is within the range, angiogenesis of the endometrium is maximally increased, endometrial blood flow rate and receptivity may be maximally increased, and thus implantation potential may be maximally increased to maximize therapeutic effect on subfertility or infertility.

Still another aspect provides a method of preventing or treating subfertility or infertility including administering the pharmaceutical composition to a subject with subfertility or infertility.

The meanings of the terms "pharmaceutical composition", "subfertility or infertility", "subject", "administration", "prevention", or "treatment" may be within the above-described range.

Advantageous Effects of Disclosure

A composition for increasing a rate of endometrial blood flow increasing a rate of endometrial blood flow, a composition for improving implantation potential, or a pharmaceutical composition according to an aspect improves embryonic implantation potential by increasing a rate of endometrial blood flow increasing a rate of endometrial blood flow just by being applied on the endometrium, and thus may be helpful to patients with subfertility or infertility, especially those who have difficulties in embryonic implantation.

Furthermore, since the composition includes botulinum toxin as an active ingredient, which is a substance that has been widely applied to the human body for cosmetic purposes, a study on the human toxicity may have a shortened period, and thus the disclosure is very useful in economical and industrial aspects.

BRIEF DESCRIPTION OF DRAWINGS

FIGS. 1 and 2 show results of RNA sequencing (RNA-seq) of the RNAs extracted from both sides of the mice uterine tissues after 8 days of treating one side of the uterus with botulinum toxin A (BoTA) and treating the other side of the uterus with saline as a control group. Among the genes changed after a BoTA treatment are genes related to angiogenesis (FIG. 1) and genes related to embryo implantation (FIG. 2) (downregulation (blue) and upregulation (red)).

MODE OF DISCLOSURE

Figure 3:
FIGS. 3 and 4 confirm similar patterns exhibited when the gene expression patterns of mice showing endometrium receptivity among the RNA-seq results performed by the same processes as in FIGS. 1 and 2 are compared with those of humans (reference: Identification of gene expression changes associated with uterine receptivity in mice, Jia-Peng He et al. Frontiers in Physiology, 2019), and show a heatmap of differentially expressed genes (DEG) based on the downregulation (green) and upregulation (red) list. Euclidian distance measurement and an average linkage clustering algorithm were used.

Hereinafter, the present disclosure will be described in more detail through examples. However, these examples are intended to illustrate the present disclosure, and the scope of the present disclosure is not limited thereto.

Example

1. Experimental Method

In order to solve the problem of implantation and pregnancy failure due to an endometrial factor, botulinum toxin A (BoTA) was injected into the uterine cavity to identify an increase of endometrial angiogenesis.

BoTA was treated by applying on the endometrium and after 8 days of BoTA treatment, expression levels of the genes related to angiogenesis and endometrial receptivity were observed. To this end, dorsal parts of the mice were incised to expose upper parts of both sides of the mice uterus, and BoTA was injected to one side by using a 1 cc syringe and the same amount of saline was injected to the other side as a control group. After the drug injection, 8 days after the incised back of the mice was stitched and recovered, both sides of uterine tissues were extracted to use in additional experiments. At this time, the botulinum toxin A used in all experiments was botulinum toxin type A provided by Hugel for free, and the unit concentration shown in the drug composition was identically applied to the experiment. Based on the application of 1 unit of botox per 1 cc of saline when applied to the human skin, a BoTA concentration used in the experiment was 0.5 unit, 1 unit, and 2 units per 1 cc of saline, and an amount of 30 µg was injected into the mice uterine cavity.

In order to identify an efficacy of BoTA on embryo implantation, pregnant mare serum gonadotropin (PMSG) was injected 7 days after the injection of BoTA/saline, hCG (human chorionic gonadotropin) was injected after 9 days, the mouse was mated with a fertile male mouse after 10 days, the uterus was extracted on the 12th day, and the numbers of implanted embryos were compared.

2. Experiment Result (1) Change of Expression of Genes Related to Angiogenesis and Embryo Implantation after Treatment of BoTA in Uterine Cavity.

In order to identify genes related to angiogenesis and embryo transplant that are differentially expressed, 573 genes differentially expressed in the BoTA-treated group in comparison to the control group were classified according to the genetic ontology. Groups related to angiogenesis (GO: 0001525, Table 1) and embryo transplant (GO: 0007566, Table 2) were classified.

TABLE 1

| Filter: 10 Gene symbol | Fold change BotoxDay 8/ Control Day 3 | P-value BotoxDay 8/ Control Day 3 | Description |
|---|---|---|---|
| Ccl7 | 7.979 | 0.029 | chemokine (C-C motif) ligand 7 |
| Cyr61 | 4.683 | 0.004 | cysteine rich protein 61 |
| Itgb3 | 2.894 | 0.002 | integrin beta 3 |
| Foxc1 | 2.803 | 0.001 | forkhead box C1 |
| Clec14a | 2.779 | 0.034 | C-type lectin domain family 14, member a |
| Hif3a | 2.153 | 0.049 | hypoxia inducible factor 3, alpha subUnit |
| Gpx1 | 2.125 | 0.026 | glutathione peroxidase 1 |
| Cd34 | 2.047 | 0.038 | CD34 antigen |
| Ccbe1 | 0.448 | 0.018 | collagen and calcium binding EGF domains 1 |
| Tgfbi | 0.326 | 0.015 | transforming growth factor, beta induced |

TABLE 2

| Filter: 4. Gene symbol | Fold change BotoxDay 8/ ControlDay 3 | P-value BotoxDay 8/ ControlDay 3 | Description |
|---|---|---|---|
| Lif | 4.021 | 0.008 | leukemia inhibitory factor |
| Itgb3 | 2.894 | 0.002 | integrin beta 3 |
| Stc2 | 2.522 | 0.033 | stanniocalcin 2 |
| Stc1 | 0.447 | 0.018 | stanniocalcin 1 |

As shown in FIGS. 1 and 2 (Tables 1 and 2), 8 days after BoTA treatment, 10 significantly differentially expressed genes were classified into angiogenesis gene oncology (GO) term. Genes classified to be upregulated were Ccl7, Cyr61, Itgb3, Foxc1, Clec14a, Hif3a, Gpx1 and Cd34, and genes classified to be downregulated were Ccbe1 and Tgfbi. Ccl7 is known to participate in macrophage recruitment which is essential for vascular remodeling through interaction with Hif-1a. Cyr61 and Itgb3 regulate angiogenesis by increasing adhesive strength of endothelial cells through interaction with each other. Foxc1 expressed by pericytes of the brain is required for endothelial proliferation and vascular remodeling in the brain. Hypoxia-inducible factors are one of the most important genes in angiogenesis that induces initiation of transcription of hypoxia-reactivity factors. The lack of glutathione peroxidase-1 is related to functional disorders of endothelial progenitor cells and causes angiogenic regulation disorders. Cd34 is known as a hematopoietic stem cell marker and is essential for inflammation and angiogenesis. Tgfbi downregulated in the BoTA-treated uterus is known to have an anti-angiogenesis and anti-cancer effect through interaction with FAS1 domain. Four significant genetic lists were classified to embryo transplant GO term: Lif, Itgb3, Stc2, and Stc1 which are a number of the most important factors in embryo transplant through activation of JAK/STAT and MAPK signal transduction and increased angiogenesis. It has been reported that during pregnancy, RNA levels of both Stc1 and Stc2 are increased in the endometrium, and Stc1 and Stc2 induction increase in the embryo transplant site. However, in decidualization, Stc1 is consistently expressed in the entire decidualization process, while Stc2 has a decreased expression at the end of the decidualization process. According to this report, Stc1 is involved in the entire decidualization process, while Stc2 may be mainly involved in the first decidualization process.

Figure 4:
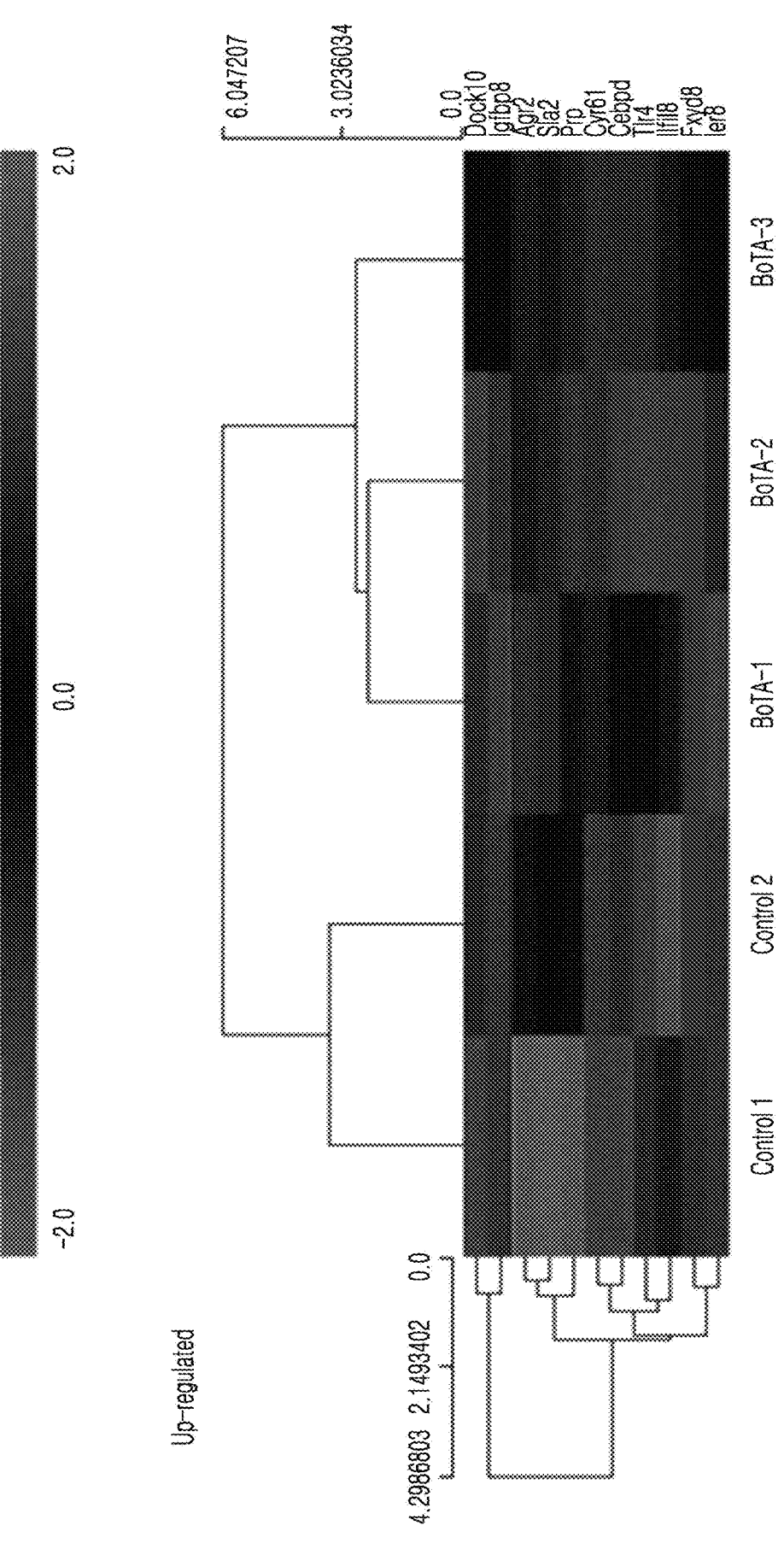

A recently reported study (reference: Identification of Gene Expression Changes Associated with Uterine Receptivity in Mice, Jia-Peng He et al. Frontiers in Physiology, 2019) identified changes of gene expression related to uterine receptivity in both humans and mice. A total of 115 differentially expressed genes were simultaneously identified in both humans and mice, and among them, 50 genes were upregulated in a receptive uterus compared to a non-receptive uterus, and 25 genes were downregulated. In order to find a correlation between our differentially expressed genes (DEG) 8 days after BoTA treatment and 115 DEGs reported in the reference, gene expression patterns of the two studies were compared. Among the 25 downregulated genes in receptive uteri of both humans and mice, 7 genes were also downregulated in our data, and 2 genes showed the opposite pattern (FIGS. 3 and 4). On the other hand, among the 50 upregulated genes in receptive uteri of humans and mice, 9 genes were upregulated in BoTA treated group compared to a control group, and 2 genes were downregulated (FIGS. 3 and 4). According to these data, it may be inferred that BoTA treatment on the uterus has a positive effect on angiogenesis, embryo transplant, and uterine receptivity.

(2) Identification of Increased Angiogenesis by BoTA Treatment in the Uterine Cavity Angiogenesis is strongly related to an increase of endometrial receptivity and regeneration of endometrial tissues.

Figure 5:
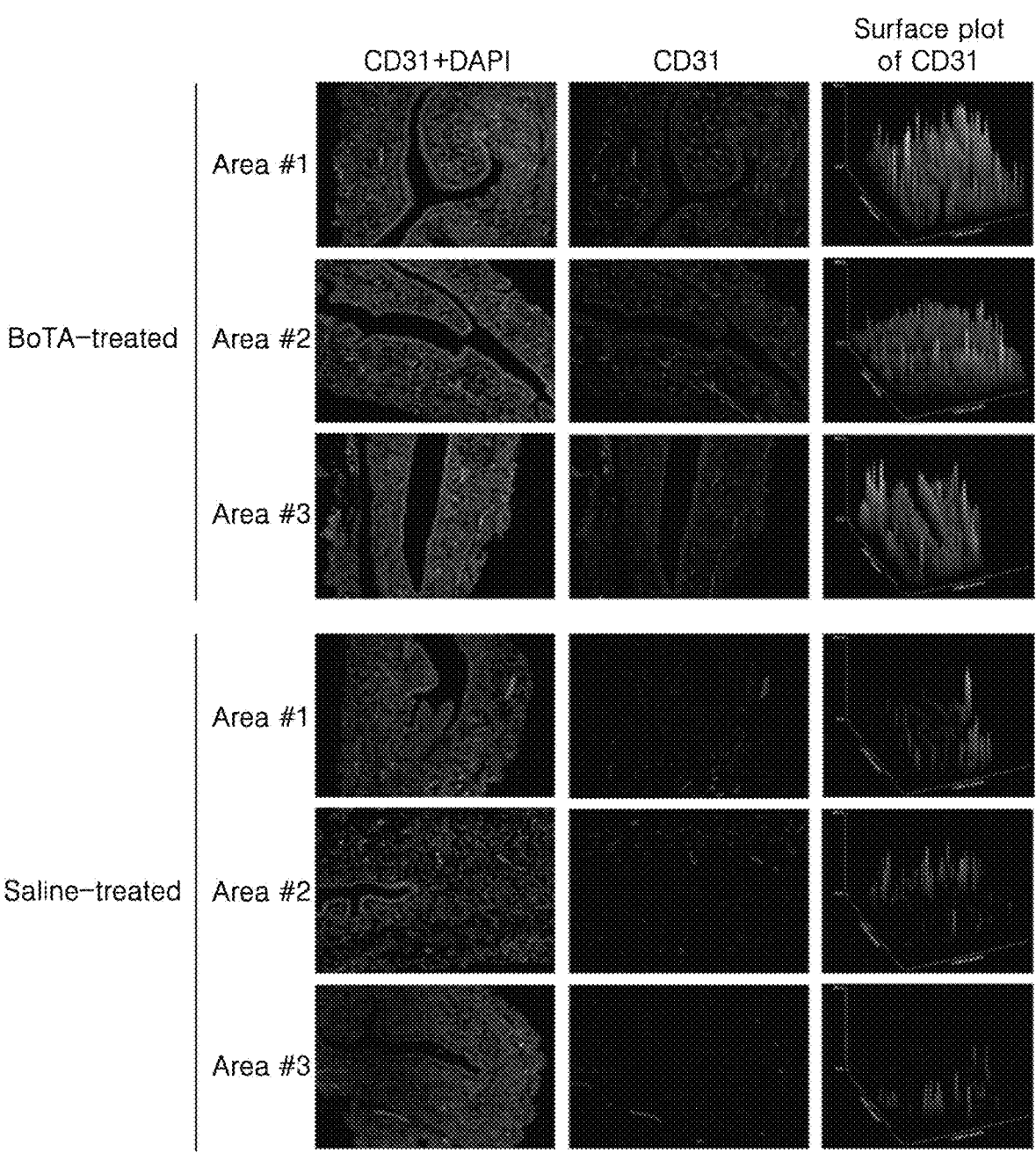
FIG. 5 is a diagram comparing the expression level of CD31 protein (red) which is an angiogenesis marker on the surface of the endometrium, in which extracted uterine tissues were sectioned (Area #1, #2, #3) after 8 days of the same drug treatment as in FIGS. 1 and 2, wherein CD31 protein expression is significantly increased in the BoTA-treated group.

As shown in FIG. 5, expression levels of CD31 protein, which is a surrogate marker for angiogenesis in immunofluorescence staining, were compared at a BoTA-treated paraffin-embedded endometrium site and a control site, and the expression level of CD31 protein in the BoTA-treated endometrial epithelial layer was significantly increased compared to the control group.

(2) Identification of Increased Embryonic Implantation Potential by BoTA Treatment in the Uterine Cavity.

Figure 6:
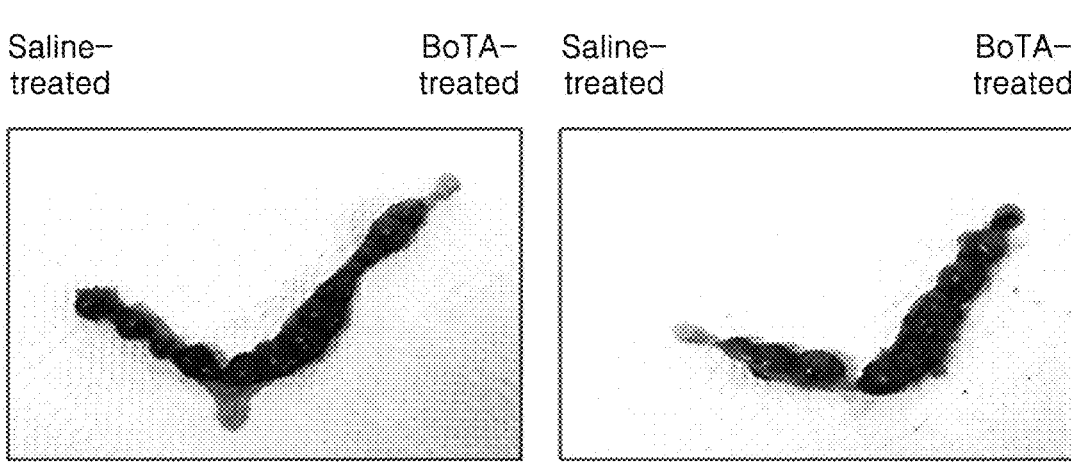
FIGS. 6 and 7 are diagrams comparing numbers of implanted embryos after treating one side of the mice uterus with BoTA and treating the other side of the uterus with saline, injecting superovulation-inducing hormone after 7 days, and mating with a fertile male after 10 days, and the number of implantations on the side treated with BoTA was shown to be significantly increased.
Figure 7:
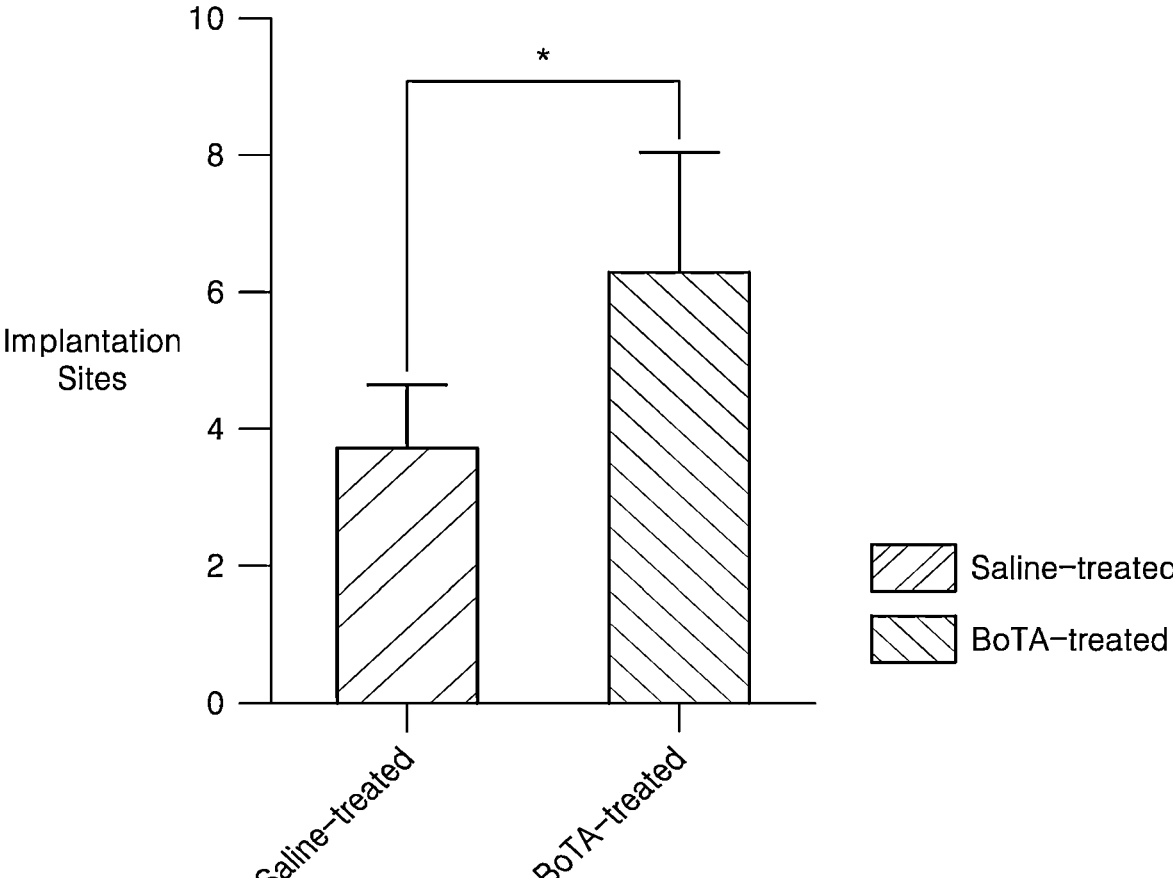

As shown in FIGS. 6 and 7, a significantly increased number of embryos implanted with clearly increased angiogenesis were identified in the BoTA-treated uterus compared to the saline-treated control group.

The invention claimed is:

1. A method of preventing or treating subfertility or infertility, the method comprising:
   administering a pharmaceutical composition to a subject with subfertility or infertility,
   wherein the pharmaceutical composition comprises botulinum toxin or a pharmaceutically acceptable salt thereof, and
   wherein the administering increases angiogenesis in an endometrium of the subject with subfertility or infertility to increase a rate of endometrial blood flow and to improve embryonic implantation potential.

2. The method of claim 1, wherein the administering increases expression of Cel7, Cyr61, Itgb3, Foxc1, Clec14a, Hif3a, Gpx1, Cd34, Lif, Itgb3, Stc2, Dll1, Cd160, Calca, Cd31, or a combination of these in the subject.

3. The method of claim 1, wherein the administering decreases expression of Ccbe1, Tgfbi, Stc1, Adra2b, Tbx4, or a combination of these in the subject.

4. The method of claim 1, wherein the botulinum toxin is botulinum toxin A.

5. The method of claim 1, wherein a concentration of the botulinum toxin or a pharmaceutically acceptable salt thereof in the pharmaceutical composition is in a range of from 0.1 to 1 unit.

6. The method of claim 1, wherein the subfertility or infertility is due to damaged endometrium, hypofunction of the uterus, recurrent pregnancy loss, recurrent failure of implantation of unknown cause, failure of implantation due to a thin endometrium, or a combination of these.

7. The method of claim 1, wherein the pharmaceutical composition comprises the salt of the botulinum toxin.

8. The method of claim 1, wherein the administering increases expression of Ccl7 these in the subject.

9. The method of claim 1, wherein the administering increases expression of Cyr61 in the subject.

10. The method of claim 1, wherein the administering increases expression of Itgb3 in the subject.

11. The method of claim 1, wherein the administering increases expression of Foxc1 in the subject.

12. The method of claim 1, wherein the administering increases expression of Clec14a in the subject.

13. The method of claim 1, wherein the administering increases expression of Hif3a in the subject.

14. The method of claim 1, wherein the administering increases expression of Gpx1 in the subject.

15. The method of claim 1, wherein the administering increases expression of Cd31 in the subject.

\*　\*　\*　\*　\*